US006514316B1

(12) United States Patent
Gaisford et al.

(10) Patent No.: US 6,514,316 B1
(45) Date of Patent: Feb. 4, 2003

(54) SYSTEM FOR IMPROVING THE MAXIMUM OPERATING TEMPERATURE AND LIFETIME OF CHROMATOGRAPHIC COLUMNS

(75) Inventors: Gregory Scott Gaisford, Denver, CO (US); David L. Walters, Fort Collins, CO (US)

(73) Assignee: MT Systems, LLC, Denver, CO (US)

(*) Notice: Subject to any disclaimer, the term of this patent is extended or adjusted under 35 U.S.C. 154(b) by 0 days.

(21) Appl. No.: 09/938,140

(22) Filed: Aug. 22, 2001

(51) Int. Cl.$^7$ .............................................. B01D 15/08
(52) U.S. Cl. ............................... 95/87; 96/101; 96/102
(58) Field of Search ......................... 95/87; 96/101–107

(56) References Cited

U.S. PATENT DOCUMENTS

| | | | |
|---|---|---|---|
| 3,309,504 A | * 3/1967 | Rosso et al. ............... 96/104 X |
| 4,050,911 A | 9/1977 | Welsh |
| 4,070,169 A | 1/1978 | Iwao et al. |
| 4,096,908 A | 6/1978 | Lamy |
| 4,181,613 A | 1/1980 | Welsh et al. |
| 4,286,456 A | * 9/1981 | Sisti et al. ............... 73/23.1 |
| 4,599,169 A | 7/1986 | Ray |
| 4,699,768 A | * 10/1987 | Weiss ..................... 96/101 X |
| 4,732,581 A | * 3/1988 | Cheh et al. ............... 95/87 |
| 4,752,216 A | 6/1988 | Hurrell |
| 4,771,628 A | 9/1988 | Sisti et al. |
| 4,948,389 A | * 8/1990 | Klein et al. ............... 95/87 X |
| 5,215,556 A | * 6/1993 | Hiller et al. ............... 95/87 |
| 5,656,170 A | * 8/1997 | Henderson ............... 95/87 X |
| 5,744,029 A | 4/1998 | Li et al. |
| 5,808,178 A | 9/1998 | Rounbehler et al. |
| 5,830,262 A | 11/1998 | Marchini et al. |
| 5,939,614 A | 8/1999 | Walters et al. |
| 6,029,498 A | 2/2000 | Walters et al. |
| 6,063,166 A | * 5/2000 | Wilson ..................... 96/102 X |
| 6,074,461 A | * 6/2000 | Wilson ..................... 96/102 |
| 6,092,921 A | 7/2000 | Gaisford et al. |
| 6,126,728 A | 10/2000 | Walsh et al. |
| 6,157,015 A | 12/2000 | Gaisford et al. |
| 6,190,613 B1 | * 2/2001 | Watanabe et al. ......... 95/87 X |
| 6,248,158 B1 | * 6/2001 | Abdel-Rahman et al. ... 95/87 X |

* cited by examiner

*Primary Examiner*—Robert H. Spitzer
(74) *Attorney, Agent, or Firm*—Dorr, Carson, Sloan & Birney, P.C.

(57) ABSTRACT

Capillary column oxidation in gas chromatography systems, particularly of polyimide clad columns, is a major cause of column failure and it limits the maximum temperature at which columns can be used. A gas chromatography column oven system is described which utilizes inert gas to substantially eliminate column oxidation thereby increasing column thermal stability. These column oven systems thus increase column lifetime and maximum operating temperature. The column oven systems comprise pneumatically sealed oven enclosures with sealed access ports, sealed sample line ports, and inlet and outlet gas ports to which are connected an inert gas supply and an exhaust gas control system respectively.

23 Claims, 5 Drawing Sheets

SYSTEM FOR IMPROVING THE MAXIMUM OPERATING TEMPERATURE AND LIFETIME OF CHROMATOGRAPHIC COLUMNS

BACKGROUND OF THE INVENTION

1. Field of the Invention

The invention relates generally to the field of gas chromatography and specifically to the design of chromatographic systems that increase the maximum operating temperature and lifetime of gas chromatograph columns.

2. Statement of the Problem

Gas chromatography is a physical method for the separation, identification, and quantification of chemical compounds. A sample mixture is injected into a flowing neutral carrier stream and the combination then flows through a tube or chromatographic column. The inner surface of the column is coated or packed with a stationary phase. As the sample mixture and carrier stream flow through the column, the components within the mixture are retained by the stationary phase to a varying degree depending on the relative volatility of the individual components and on their respective affinities for the stationary phase. When the individual mixture components are released into the carrier stream by the stationary phase, they are swept towards the column outlet where they are detected and measured with a detector. Different chemical compounds are retained for different times by the stationary phase. The specific compounds in the mixture can be identified and their relative concentrations determined by measuring peak retention times and peak areas respectively.

Gas chromatograph (GC) measurements are facilitated by the application of heat to the chromatographic column to change its temperature. The use of heated column ovens in GC systems greatly increases the number of compounds that can be analyzed and reduces the time required for each analysis by increasing the volatility of higher molecular weight compounds.

Many methods have been described for heating chromatographic columns. The most commonly used methods utilize air bath ovens that circulate heated air through a thermally insulated chamber in which a chromatographic column is placed. Once an analysis has been completed, cold ambient air is circulated through these ovens to cool them. Air bath ovens typically utilize large fans and/or moving baffles to control the flow of warm or cold air through the oven enclosure and thereby control the temperature of the column. U.S. Pat. No. 4,050,911 to Welsh, U.S. Pat. No. 4,070,169 to Iwao et. al., U.S. Pat. No. 4,096,908 to Lamy, U.S. Pat. No. 4,181,613 to Welsh et. al., U.S. Pat. No. 4,599,169 to Ray, U.S. Pat. No. 4,752,216 to Hurl, U.S. Pat. No. 4,771,628 to Sisti et. al., U.S. Pat. No. 5,744,029 to Li et. al., U.S. Pat. No. 5,830,262 to Marchini et. al., and U.S. Pat. No. 6,126,728 to Walsh et. al. describe different types of GC air bath ovens.

Polyimide coated, fused silica capillary columns are the most commonly used columns in gas chromatography. They are strong, flexible, and lightweight. They can often be used for thousands of analyses. However, in existing gas chromatographs these columns are not suitable for analyses above 350° C. because the polyimide coating rapidly oxidizes above 350° C. making the columns brittle. Hydrocarbon separations of molecules containing in excess of 50 carbon atoms are generally performed at temperatures exceeding 350° C. For these high temperature analyses, chemists must either frequently replace polyimide columns that break after tens of analyses or use significantly more expensive metal clad columns. Even at temperatures below 350° C., the lifetime of polyimide-coated fused silica columns is reduced by polyimide oxidation in an oxygen environment.

In the absence of oxygen, the thermal stability of polyimide is substantially enhanced thereby significantly increasing its maximum useful operating temperature. The lifetime of polyimide can be increased by over an order of magnitude at high temperature in an oxygen-free environment. This can in turn dramatically increase the maximum operating temperature and lifetime of polyimide-coated GC columns. However, it is not practical with commercially available GC column oven technology to heat columns in an oxygen-free (inert gas) environment. Conventional ovens are designed to utilize vast volumes of circulating atmospheric air to heat and cool columns.

Complete process GC's are often built within purged, explosion proof cabinets. A positive barometric pressure is typically maintained within these cabinets to prevent the ingress of potentially explosive gas from an external industrial environment. These purged cabinets are pneumatically connected to a source of pressurized, clean (non-explosive) air that maintains the pressure within the cabinet at a level above the prevailing atmospheric pressure. Because these cabinets are generally large and because inert gas is expensive as compared to clean air, inert gas is not generally used to purge explosion proof process GC cabinets. Moreover, oven/column cool down times are generally poor in enclosed, purged GCs because vast volumes of cold air are not readily available to cool down the column ovens. As most process GC's keep the column oven at a fixed temperature, cooling time limitations are unimportant. However, for the broad range of GC's and analyses that utilize temperature cycling, slow cool down is a problem. It results in fewer analyses per day, thus increasing costs. Maintaining a complete GC within a purged, inert gas filled cabinet is not a practical method for increasing the high temperature durability of polyimide coated columns. This solution is more expensive than is the problem.

Some GC column ovens have been described which are pneumatically sealed from the atmosphere outside the oven enclosure. See for example, U.S. Pat. No. 4,286,456 to Sisti et. al. and U.S. Pat. Nos. 6,093,921 and 6,157,015 to Gaisford et. al. None of these devices, however, can maintain an inert gas environment around the column within the column oven enclosure.

3. Solution

Pneumatically sealing a column oven enclosure isolates the interior of the oven enclosure from the atmosphere outside the enclosure. Filling the sealed oven enclosure with inert gas results in an oxygen free environment within the oven enclosure. Polyimide coated, GC columns heated in such an oven enclosure will last much longer at elevated temperatures and can be used at higher temperatures than can the same columns in conventional GC column ovens. Furthermore, suitably designed column oven systems achieve cooling times at least as fast as those of conventional GC ovens using only modest volumes of inert gas.

SUMMARY OF THE INVENTION

The present invention provides a gas chromatography system that maintains an inert gas within an oven enclosure during the heating process. The system comprises a pneumatically sealed oven enclosure, an inert gas supply, and an exhaust gas control system. The oven enclosure includes a sealed access port through which columns can be installed, two sealed sample line ports through which sample lines enter and exit the oven enclosure, and two gas ports through which gas may enter or exit the oven enclosure.

It is the object of the invention to provide a gas chromatograph system that increases the maximum operating temperature of a gas chromatographic column.

It is the object of the invention to provide a gas chromatograph system that increases the lifetime of a gas chromatographic column.

It is the object of the invention to provide a gas chromatograph system that pneumatically isolates the interior of an oven enclosure from its exterior.

It is the object of the invention to provide a gas chromatograph system that heats a gas chromatographic column in an inert gas environment.

It is the object of the invention to provide a gas chromatograph system that maintains an oxygen free environment within a column oven by maintaining a positive pressure of inert gas within the oven enclosure.

It is the object of the invention to provide a gas chromatograph system that uses cool, flowing inert gas to accelerate the cooling rate of a column.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Figure 1:
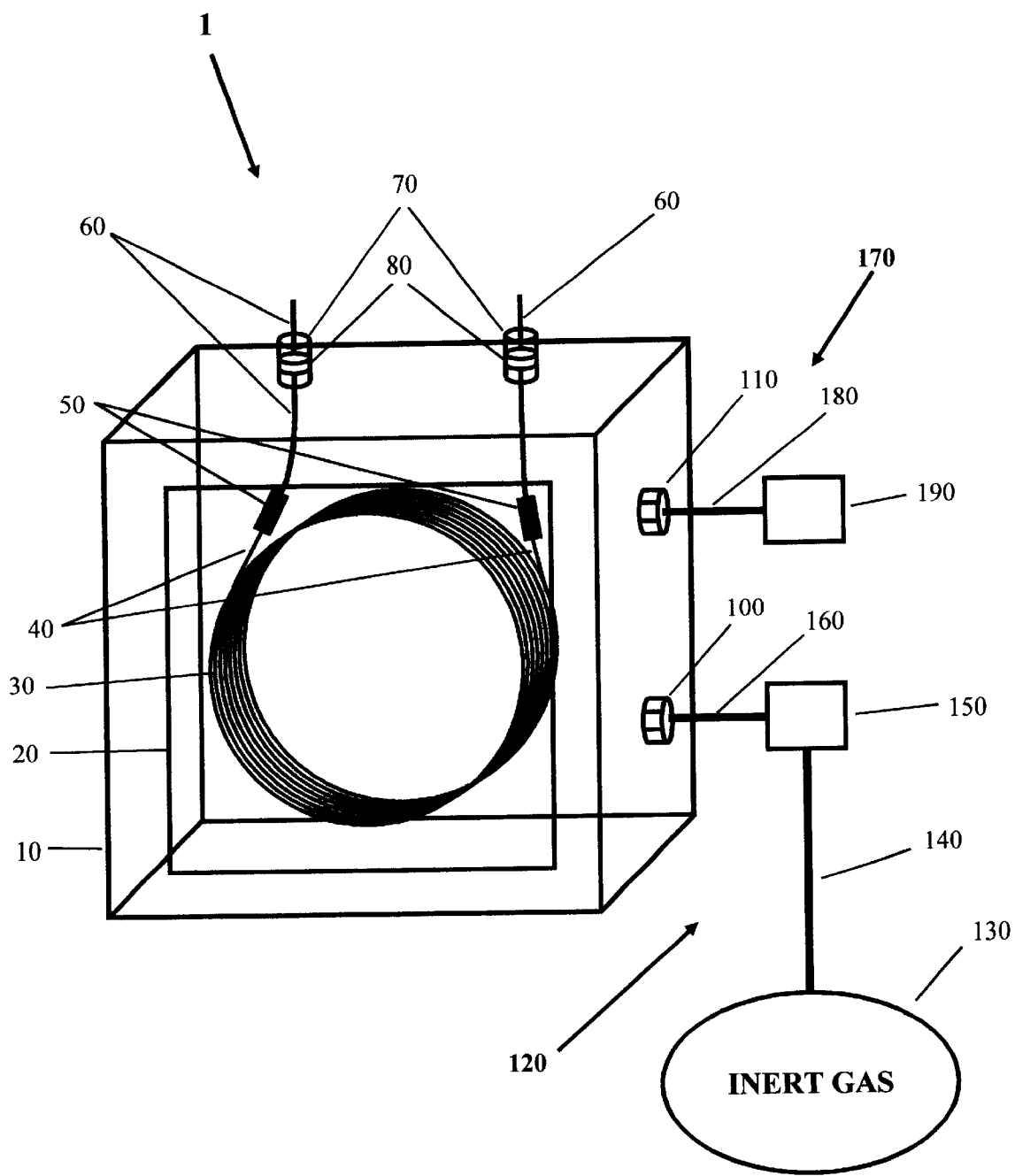
FIG. 1 shows a perspective view of a gas chromatograph column oven system constructed in accordance with the present invention in which a column is heated in an inert gas environment.

FIG. 1 shows GC column oven system 1 that maintains an inert gas within the oven enclosure 10 when it is heated. The oven enclosure 10 is any container that physically delimits an inner volume of space from the exterior of the container. The interior of the oven enclosure 10 is pneumatically sealed from the exterior so as to prevent the flow of gas from the exterior into the interior of the oven enclosure 10. The exact shape of the oven enclosure 10 and the manner in which it is sealed are not material to the invention described herein. The oven enclosure 10 contains at least one door or access port 20 through which a user can access the inside of the oven enclosure 10 for service or to install a column. When closed, the access port 20 is pneumatically sealed so that gas external to the oven enclosure 10 does not enter the oven enclosure 10 through the door nor through the gap between the edges of the access port 20 and the walls of the oven enclosure 10. The column 30 is contained within the oven enclosure 10.

Two sample line ports 70 are provided in the walls of the oven enclosure 10 through which sample line tubes carrying the chemical sample to be analyzed by the GC enter and exit the oven enclosure 10. The sample tubes may be the column ends 40 of column 30 or separate transfer lines 60. If transfer lines 60 are used as is shown in FIG. 1, the ends of the two transfer lines 60 within the oven enclosure 10 are pneumatically connected to the column ends 40 with column unions 50. The transfer lines 60, the column unions 50, and the column 30 comprise a single, pneumatically sealed sample tube through which chemical samples and carrier gas can flow freely from one end to the other without contaminating or being contaminated by the gaseous atmosphere within the oven enclosure 10. The sample line ports 70 include sample line seals 80 that substantially prevent the flow of external ambient air into the oven enclosure 10 through the sample line ports 70.

Two gas ports, inlet gas port 100 and outlet gas port 110, are provided in the walls of the oven enclosure 10 through which gas may flow into and out of the interior of the oven enclosure 10. Inlet gas port 100 is connected to inert gas supply 120 such that inert gas can flow into and fill the oven enclosure 10. Inert gas shall refer herein to any gas or gas mixture that is substantially free of oxygen such as nitrogen, carbon dioxide, helium, neon, or argon. The inert gas supply 120 shall comprise any combination of equipment that together supply inert gas at a pressure higher than that of the interior of the oven enclosure 10. For example and as shown in FIG. 1, the inert gas supply 120 may comprise pressurized inert gas reservoir 130, flow line 140, the flow controller 150, and flow line 160 that are connected in series and through which inert gas flows. The inert gas reservoir 130 is any pressurized tank, bottle, or equivalent container of inert gas. For the purposes of this invention, a flow controller shall be any device or combination of devices that can be used to measure, regulate, or control the flow of gas in a flow line including pressure sensors, valves, flow meters, and flow regulators. The gas outlet port 110 is connected to the gas exhaust system 170. The gas exhaust system 170 shall comprise any combination of equipment that together controls the flow of gas from the oven enclosure 10. For example and as shown in FIG. 1, the gas exhaust system 170 comprises the flow line 180 and the flow controller 190 that are connected in series and through which gas can flow from the oven enclosure 10 in a regulated manner.

When a column 30 is installed into the oven enclosure 10, the access port 20 must be opened resulting in oxygen contamination within the oven enclosure 10. To prevent unnecessary waste of inert gas while the access port 20 is open, flow controller 150 stops the flow of inert gas into oven enclosure 10. After the column 30 is installed and the access port 20 closed, oxygen in the oven enclosure 10 must be substantially removed prior to heating the column 30. Oxygen can be purged from the oven enclosure 10 by simultaneously opening the flow controllers 150 and 190 and allowing inert gas to freely flow through the oven enclosure 10 until the oxygen is substantially removed. Alternatively, the flow controllers 150 and 190 can be opened asynchronously. First, the first flow controller 150 is opened and the second flow controller 190 is closed which effectively pressurizes the oven enclosure 10. Inert gas mixes with the atmospheric gas contained therein. Second, the first flow controller 150 is closed and the second flow controller 190 is opened allowing the pressurized gas mixture to flow from the oven enclosure 10. By repeating this process, the oxygen in the oven enclosure 10 is rapidly diluted and effectively eliminated.

Inert gas can be used to speed up the cooling cycle after a heating cycle is completed. Opening the flow controllers 150 and 190 either synchronously or asynchronously during the cooling cycle allows cool inert gas from the inert gas supply 120 to flow through the oven enclosure 10 thereby accelerating the cooling rate of the column 30 contained therein. Alternatively, cool ambient air could be circulated through the oven enclosure 10 to cool it down. Using ambient air could reduce the volume of inert gas needed to operate the GC column oven systems taught herein that utilize accelerated cooling methods.

Once an inert gas environment is established within the oven enclosure 10, it can be maintained without contamination in one of two ways. First, the interior of the oven enclosure 10 can be completely sealed from its exterior so that no unwanted gas flows into or out of the oven enclosure 10. In practice, it may be difficult to achieve a perfect pneumatic seal. With an imperfect seal, oxygen could slowly leak into the oven enclosure 10 from the atmosphere and contaminate the inert gas environment contained therein. A second method for preventing oxygen contamination is to use the flow controller 150 in the inert gas supply 120 to maintain a positive pressure (with respect to the atmospheric pressure) of inert gas within the oven enclosure 10. Maintaining a positive pressure within oven enclosure 10 ensures that oxygen does not leak into the oven enclosure 10 even if there were small pneumatic leaks in the oven enclosure 10. The flow of gas would at all times be from the interior of the oven enclosure 10 to the exterior. For the purposes of this invention, the oven enclosure 10 shall be considered pneumatically sealed even if it contains small leaks provided that a) the leakage rate of oxygen into the oven is not large enough to substantially increase the degradation of the column 30 and/or b) the leakage rate of inert gas from a positively pressured oven enclosure 10 is not large enough to substantially increase the volume of inert gas required to maintain the inert gas environment within the oven enclosure 10.

During the heating cycle, the gas within the oven enclosure 10 will increase in temperature. If the oven enclosure 10 is pneumatically sealed, the pressure within the oven enclosure 10 could increase during the heating cycle. This pressure can be relieved using the flow controller 190 within the gas exhaust system 170. The flow controller 190 can release gas when the internal pressure of the oven enclosure 10 exceeds a threshold value, thus limiting the maximum potential pressure within the oven enclosure 10. If cooling gas is not circulated through the oven enclosure 10 during the cooling cycle to accelerate cooling, then the pressure within the oven enclosure 10 would similarly decrease as the temperature of the inert gas within the oven enclosure 10 decreases. This could result in a negative pressure (with respect to atmospheric pressure) forming within the oven enclosure 10 drawing oxygen into the oven. Using the flow controller 150 to maintain a positive pressure within the oven enclosure 10 prevents this potential oxygen ingress when the oven is cooling.

Heaters, fans, baffles, or other devices well known in the art may be added to the GC column oven system 1 to enable heating capabilities, to improve cooling rates, or to otherwise improve operating performance. However, such additional equipment is not an essential part of the invention taught herein and as such is not described. As should be clear to those skilled in the art, any such device can be added to the GC column oven system 1 provided that care is taken where appropriate to utilize pneumatic seals to substantially prevent oxygen ingress into the oven enclosure 10 while it or the column 30 is being heated.

Typical chromatographic columns are mounted on cylindrical fixtures that are 15 to 20 cm in diameter and up to 7 cm in height. An oven enclosure 10, like that shown in FIG. 1, built to accommodate such column fixtures would have an internal volume in excess of 5 liters. Such an oven enclosure requires substantial volumes of inert gas to purge oxygen from the enclosure after a column is installed or to cool down after a heating cycle is completed. A smaller oven enclosure reduces the volume of inert gas needed to purge the enclosure after a column change. A smaller oven enclosure also reduces the thermal mass of the system and thereby reduces the consumption of inert gas that would be needed to cool the system down. To make the oven enclosure smaller, the chromatographic column must be smaller.

Figure 2:
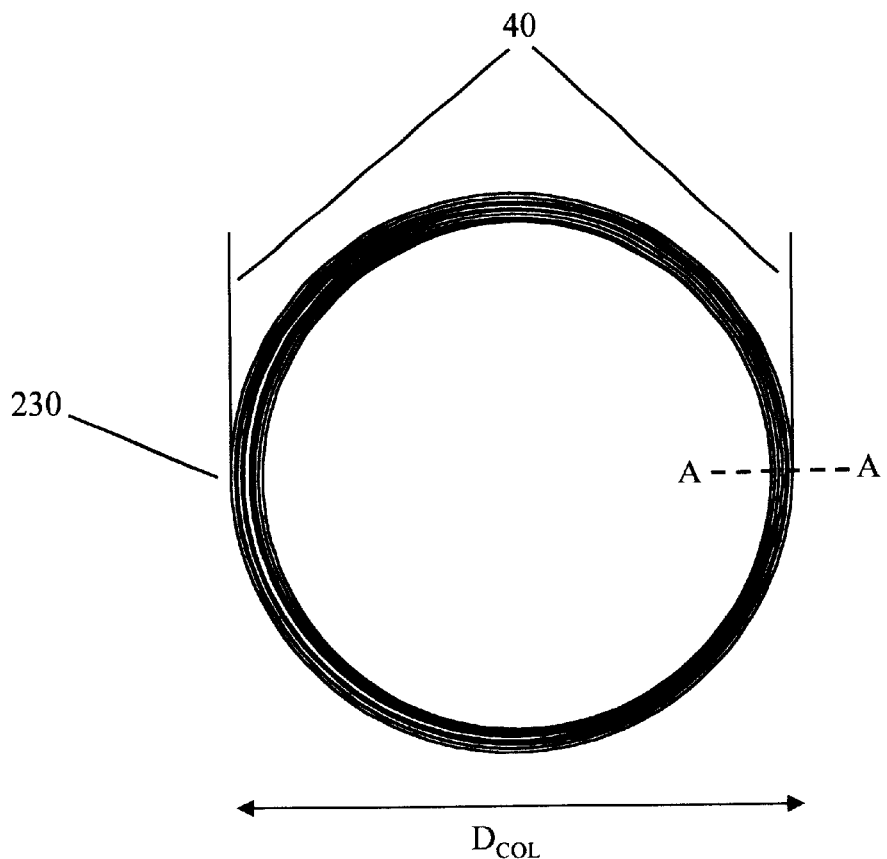
FIG. 2 shows a tightly wound chromatographic column bundle.
Figure 3:
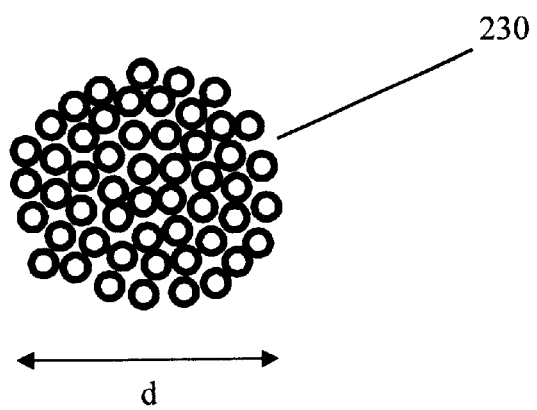
FIG. 3 shows the cross-section of a tightly wound column bundle.

FIG. 2 shows a column bundle 230 where a chromatographic column is wound tightly together to form a bundled coil and thereby minimize its physical size. FIG. 3 shows a view of the column bundle 230 across the section marked A—A in FIG. 2. A 30 m, 0.32 $\mu$m ID column coiled in the manner illustrated in FIG. 2 could have a major diameter '$D_{COL}$' of less than 8 cm and a cross sectional diameter 'd' of less than 6 mm. It shall be understood that the exact geometry of the column bundle 230 is not a critical aspect of this invention. Column bundle 230 shall refer to any chromatographic column packaged to achieve a small physical size.

Figure 4:
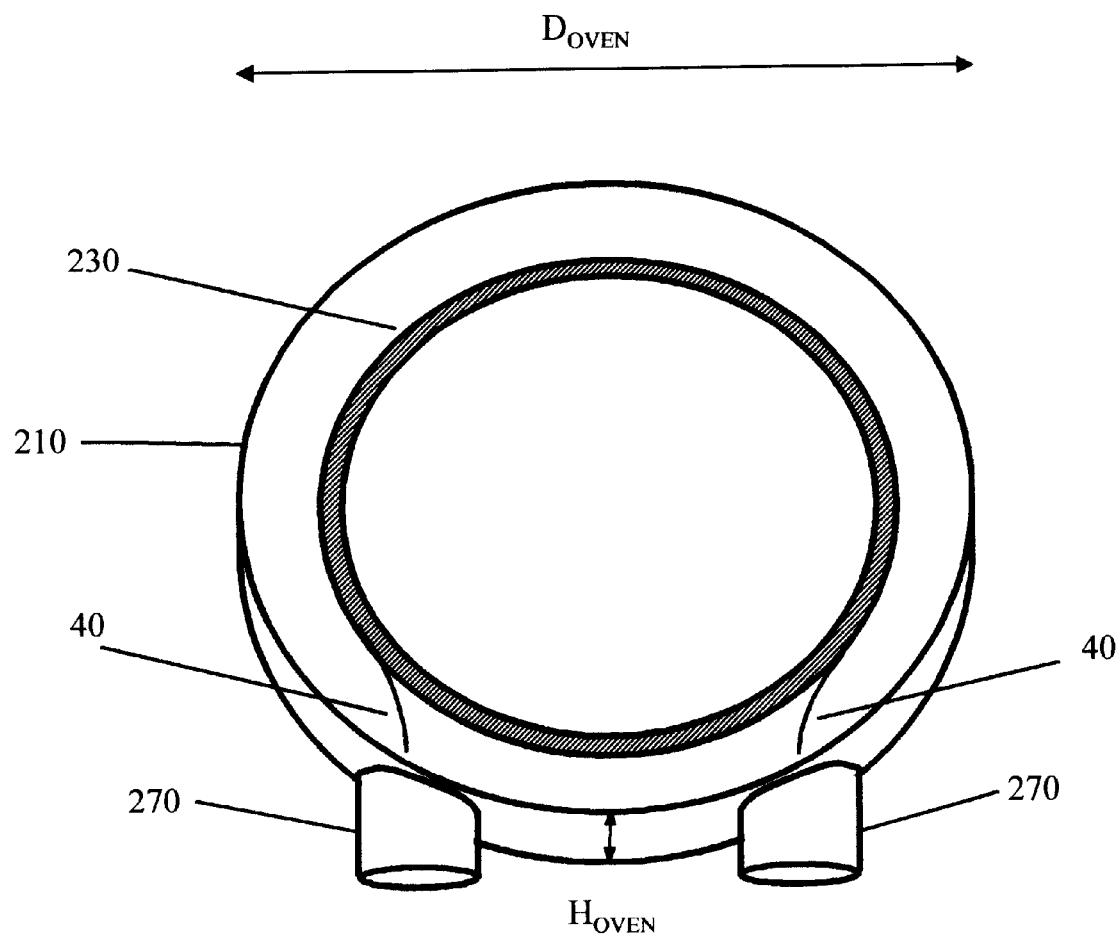
FIG. 4 shows a perspective view of an oven enclosure and a tightly wound column bundle.

FIG. 4 shows an oven enclosure 210 having a substantially annular cavity that can be used to contain and heat the column bundle 230. The oven enclosure 210 could have an internal diameter '$D_{OVEN}$' of less than 10 cm and an internal height '$H_{OVEN}$' of less than 1.5 cm resulting in an internal volume of less than 0.12 liters. The precise shape of the oven enclosure 210 is not an essential feature of this invention. The oven enclosure 210 can be any compact, pneumatically sealed enclosure designed to take advantage of the small size of the column bundle 230 contained therein and thereby reduce the volume of inert gas needed to operate the GC column oven system.

Figure 5:
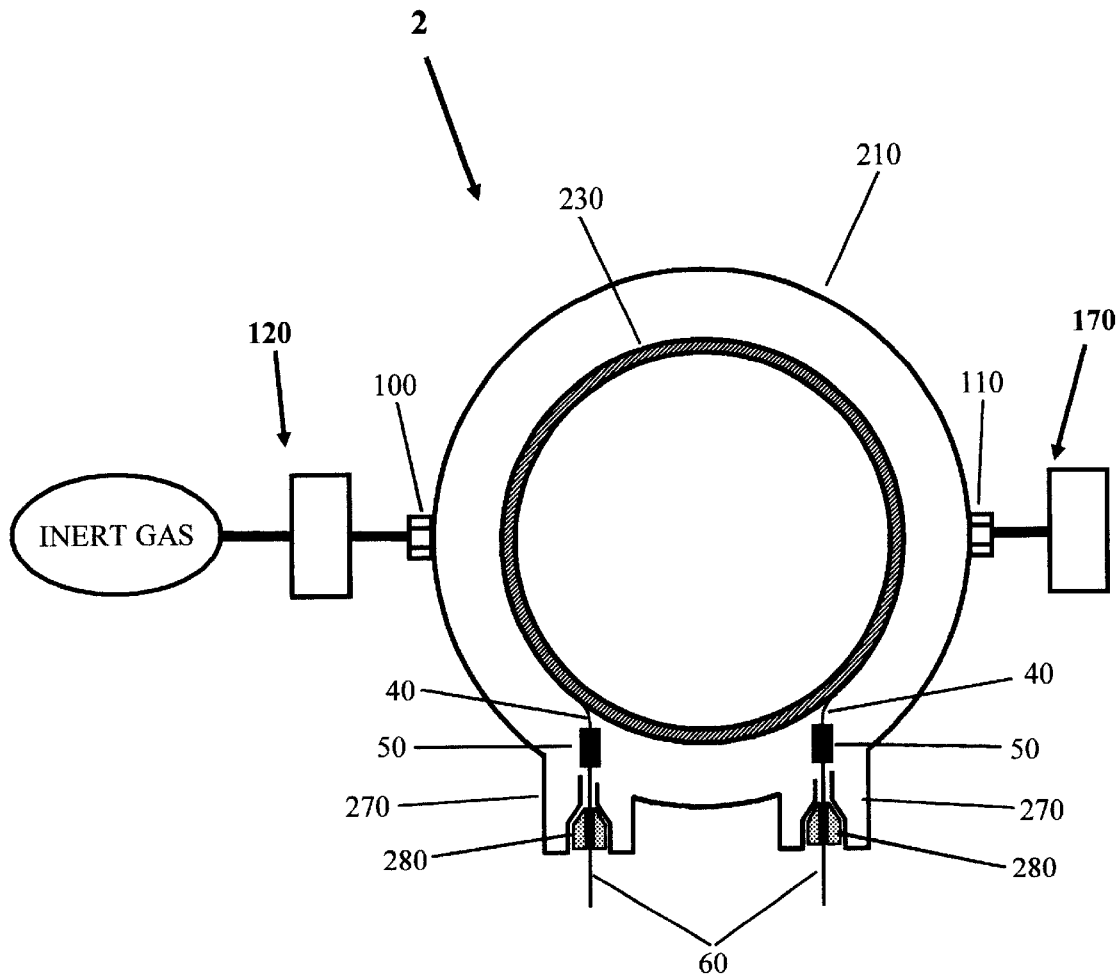
FIGS. 5 and 6 show two different cross sectional views of a gas chromatograph column oven system constructed in accordance with the present invention in which a tightly wound column bundle is heated in an inert gas environment.
Figure 6:
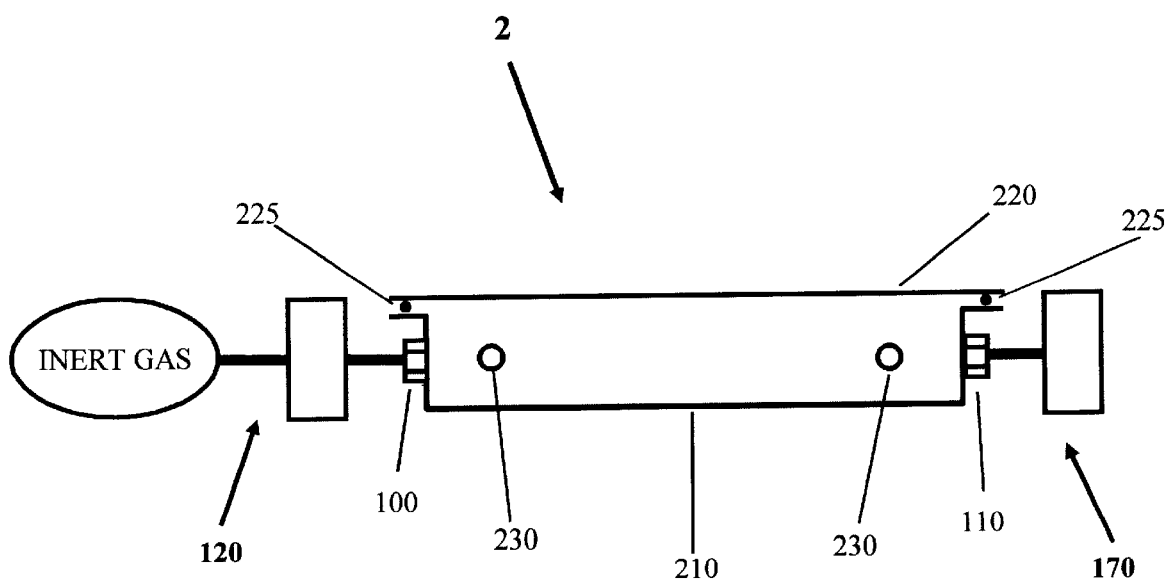

FIGS. 5 and 6 are orthogonal, cross sectional views of a preferred embodiment of this invention. The GC column oven system 2 includes the oven enclosure 210 and the column bundle 230 as shown in FIG. 4. The oven enclosure 210 has an access port 220 that can be removed such that a user can access the inside of the oven enclosure 210 for service or to install the column bundle 230. The pressure seal 225, placed between the access port 220 and the oven enclosure 210, provides a pneumatic seal between the two. The pressure seal 225 can be any suitable sealing device such as an elastomeric o-ring.

Two sample line ports 270 are provided in the walls of the oven enclosure 210 through which sample lines can enter or exit through the wall of the oven enclosure 210. The sample line ports 270 contain sample line seals 280 that substantially prevent the flow of external ambient air into the oven enclosure 210 through the sample line ports 270. The sample line seals 280 can be any suitable sealing devices such as ferrules. As is shown in FIGS. 5 and 6, two transfer lines 60 enter oven enclosure 210 through the sample line ports 270 and the sample line seals 280. The transfer lines 60 are connected to the column ends 40 of the column bundle 230 with column unions 50 such that the combination comprises a single, pneumatically sealed sample tube through which chemical samples and carrier gas can flow freely from one end to the other without contaminating or being contaminated by the gaseous atmosphere within the oven enclosure 210.

Gas inlet port 100 and gas outlet port 110 are provided in the walls of the oven enclosure 210 and provide means through which gas can flow in and out of the oven enclosure 210. Inert gas supply 120 is connected to the gas inlet port 100 and supplies inert gas to the interior of the oven enclosure 210. Gas exhaust system 170 is connected to the gas outlet port 120 and controls the flow of gas out of the oven enclosure 210.

The effective thermal mass of the GC column oven system 2 can be further reduced if the thermal energy in the heating system is deposited directly in the column bundle 230 and not into the oven enclosure 210 because the column bundle 230 has much less thermal mass. If the oven enclosure 210 is also thermally isolated from the column bundle 230, it stays cool even when the column bundle 230 is hot. In such a configuration, the primary function of the oven enclosure 210 is to pneumatically isolate the column bundle 230 from oxygen and not to provide a means to heat the column bundle 230.

A chromatographic column can be directly heated in a variety of ways independently of the oven enclosure 210 and coiled into the column bundle 230 illustrated in FIGS. 2 and 3. The column could be heated by a resistively heated wire that is coiled up together with the column in the column bundle 230 shown in FIG. 2. The column could be enclosed within a metal sheath that resistively heats the column. The column/metal sheath can be coiled tightly in the manner illustrated in FIG. 2. The column could have microwave absorber embedded into it so that it could be directly heated by microwave energy. Many methods known to those skilled in the art can be used to directly heat a chromatographic column substantially independently of the column oven enclosure.

The exact method by which a column is heated is not a critical aspect of the invention taught herein. For the purposes of this invention, it shall be understood that the oven enclosure 210 shall refer to any physical enclosure used to pneumatically isolate the column bundle 230 from the atmosphere exterior to the oven enclosure 210. The oven enclosure 210 may or may not be part of the systems used to heat the column bundle 230. It shall also be understood that the column bundle 230 shall refer to any tightly bundled column or column/heater combination designed to achieve small size. The column bundle 230 may include direct heating means such as microwave absorbers or resistively heated wires or sheaths without deviating from the teaching of this patent.

When direct column heating means are utilized, the column bundle 230 can be passively cooled as quickly as a column can be cooled using active, convective cooling in conventional GC column ovens. Direct dissipation to the environment is fast enough to shed the minimal thermal energy in the column bundle 230. Even faster cooling rates can be achieved with small volumes of inert gas flowing into the oven enclosure 210 during cooling cycles. Thus, the GC column oven system 2 can significantly enhance the maximum operating temperature and lifetime of the column without sacrificing cooling rates using only modest volumes of inert gas.

The above disclosure sets forth a number of embodiments of the present invention. Specifically, the above disclosure addresses GC column oven systems that comprise pneumatically sealed column oven enclosures filled with inert gas to substantially improve the maximum operating temperature and lifetime of chromatographic columns. Other arrangements or embodiments, not precisely set forth, could be practiced under the teachings of the present invention and as set forth in the following claims.

We claim:

1. A method of operation for a chromatography system having a heating cycle and a cooling cycle for processing a series of samples through a chromatography column within a pneumatically-sealable oven enclosure, said method comprising:
    filling the oven enclosure with an inert gas substantially devoid of oxygen to purge oxygen from within the oven enclosure prior to the heating cycle;
    maintaining a substantially oxygen-free atmosphere within the oven enclosure during the heating cycle;
    inducing a flow of a cooling gas through the oven enclosure during the cooling cycle.

2. The method of claim 1 wherein the inert gas comprises nitrogen.

3. The method of claim 1 wherein the inert gas comprises carbon dioxide.

4. A chromatography system comprising:
    an oven having a pneumatically-sealable interior enclosure;
    a chromatographic column within the oven enclosure; and
    a gas supply for supplying gas substantially devoid of oxygen to the oven enclosure surrounding the chromatographic column to thereby purge oxygen from within the oven enclosure.

5. The chromatography system of claim 4 wherein the gas comprises nitrogen.

6. The chromatography system of claim 4 wherein the gas comprises carbon dioxide.

7. The chromatography system of claim 4 wherein the chromatographic column comprises a bundled coil.

8. The chromatography system of claim 7 wherein the oven enclosure has a substantially annular cavity to contain the coil.

9. The chromatography system of claim 4 further comprising a gas supply flow controller regulating the flow of gas from the gas supply into the oven enclosure.

10. The chromatography system of claim 9 wherein the gas supply flow controller maintains the oven enclosure at a positive pressure to prevent diffusion of oxygen into the oven enclosure.

11. The chromatography system of claim 9 further comprising an exhaust system having a exhaust flow controller regulating the flow of gas from the oven enclosure.

12. The chromatography system of claim 11 wherein the exhaust flow controller releases gas from the oven enclosure if the pressure within the oven enclosure exceeds a predetermined limit.

13. The chromatography system of claim 11 having a heating cycle and a cooling cycle for processing samples, and wherein the gas supply flow controller and exhaust flow controller regulate the flow of gas through the oven enclosure to purge oxygen from within the oven enclosure prior to the heating cycle.

14. The chromatography system of claim 11 having a heating cycle and a cooling cycle for processing samples, and wherein the gas supply flow controller and exhaust flow controller regulate the flow of gas through the oven enclosure to accelerate cooling of the column during the cooling cycle.

15. A chromatography system having a heating cycle and a cooling cycle for processing a series of samples, said chromatography system comprising:
    an oven having a pneumatically-sealable interior enclosure;
    a chromatographic column within the oven enclosure;

a gas supply for supplying gas substantially devoid of oxygen;

a gas supply flow controller regulating the flow of gas from the gas supply into the oven enclosure prior to the heating cycle to thereby purge oxygen from within the oven enclosure; and an exhaust system having a exhaust flow controller for regulating the flow of gas from within the oven enclosure during the cooling cycle.

16. The chromatography system of claim 15 wherein the gas comprises nitrogen.

17. The chromatography system of claim 15 wherein the gas comprises carbon dioxide.

18. The chromatography system of claim 15 wherein the chromatographic column comprises a bundled coil.

19. The chromatography system of claim 18 wherein the oven enclosure has a substantially annular cavity to contain the coil.

20. The chromatography system of claim 15 wherein the gas supply flow controller and exhaust flow controller regulate the flow of gas through the oven enclosure to purge oxygen from within the oven enclosure prior to the heating cycle.

21. The chromatography system of claim 15 wherein the gas supply flow controller and exhaust flow controller regulate the flow of gas through the oven enclosure to accelerate cooling of the column during the cooling cycle.

22. The chromatography system of claim 15 wherein the gas supply flow controller maintains the oven enclosure at a positive pressure to prevent diffusion of oxygen into the oven enclosure.

23. The chromatography system of claim 15 wherein the exhaust flow controller releases gas from the oven enclosure if the pressure within the oven enclosure exceeds a predetermined limit.

* * * * *